US011432775B2

(12) United States Patent
Jang et al.

(10) Patent No.: US 11,432,775 B2
(45) Date of Patent: Sep. 6, 2022

(54) APPARATUS AND METHOD FOR ESTIMATING BLOOD PRESSURE

(71) Applicants: SAMSUNG ELECTRONICS CO., LTD., Suwon-si (KR); UNIVERSITY OF MARYLAND, COLLEGE PARK, College Park, MD (US)

(72) Inventors: Dae Geun Jang, Yongin-si (KR); Peyman Yousefian, College Park, MD (US); Jin-Oh Hann, Potomac, MD (US); Ui Kun Kwon, Hwaseong-si (KR); Youn Ho Kim, Hwaseong-si (KR); Sungtae Shin, Greenbelt, MD (US)

(73) Assignees: SAMSUNG ELECTRONICS CO., LTD., Suwon-si (KR); University of Maryland, College Park, College Park, MD (US)

( * ) Notice: Subject to any disclaimer, the term of this patent is extended or adjusted under 35 U.S.C. 154(b) by 117 days.

(21) Appl. No.: 16/589,260

(22) Filed: Oct. 1, 2019

(65) Prior Publication Data
US 2020/0196959 A1 Jun. 25, 2020

(30) Foreign Application Priority Data
Dec. 21, 2018 (KR) .................. 10-2018-0167746

(51) Int. Cl.
*A61B 5/021* (2006.01)
*A61B 5/00* (2006.01)
*A61B 5/11* (2006.01)

(52) U.S. Cl.
CPC ........ *A61B 5/7278* (2013.01); *A61B 5/02125* (2013.01); *A61B 5/1102* (2013.01);
(Continued)

(58) Field of Classification Search
CPC . A61B 5/7278; A61B 5/02125; A61B 5/1102; A61B 5/681; A61B 5/7264;
(Continued)

(56) References Cited

U.S. PATENT DOCUMENTS 8,983,854 B2 3/2015 Park et al.
10,786,161 B1 * 9/2020 Archdeacon ......... A61B 5/7278
(Continued)

FOREIGN PATENT DOCUMENTS

KR 10-2010-0059198 A 6/2010
KR 10-2014-0116347 A 10/2014
(Continued)

OTHER PUBLICATIONS

Garg et al., "Vertical Mode Human Body Vibration Transmissibility," IEEE Transactions on Systems, Man, and Cybernetics, vol. SMC-6, No. 2, Feb. 1976, pp. 102-112, 11 pages total.
(Continued)

*Primary Examiner* — Navin Natnithithadha
(74) *Attorney, Agent, or Firm* — Sughrue Mion, PLLC

(57) ABSTRACT

An apparatus for estimating blood pressure includes: a ballistocardiogram (BCG) sensor configured to measure a limb BCG signal from a user; and a processor configured to obtain blood pressure-related features from the measured limb BCG signal, according to sensing characteristics of the BCG sensor, and estimate a blood pressure of the user based on the obtained blood pressure-related features.

15 Claims, 13 Drawing Sheets

(52) U.S. Cl.
CPC ............ *A61B 5/681* (2013.01); *A61B 5/7264* (2013.01); *A61B 5/7289* (2013.01); *A61B 2560/0223* (2013.01); *A61B 2562/0219* (2013.01)

(58) Field of Classification Search
CPC .......... A61B 5/7289; A61B 2560/0223; A61B 2562/0219; A61B 5/352; A61B 5/0261; A61B 5/7246; A61B 5/7267; A61B 5/7275; A61B 5/021
See application file for complete search history.

(56) References Cited

U.S. PATENT DOCUMENTS

| | | | |
|---|---|---|---|
| 2010/0016680 A1* | 1/2010 | Addison | A61B 5/726 600/301 |
| 2010/0210921 A1 | 8/2010 | Park et al. | |
| 2015/0018637 A1* | 1/2015 | Chen | A61B 5/0295 600/301 |
| 2015/0112606 A1 | 4/2015 | He et al. | |
| 2016/0220122 A1 | 8/2016 | Luna et al. | |
| 2016/0317043 A1 | 11/2016 | Campo et al. | |
| 2017/0188968 A1* | 7/2017 | Banet | A61B 5/14552 |
| 2017/0238847 A1* | 8/2017 | Inan | A61B 5/6823 |
| 2017/0273635 A1 | 9/2017 | Li et al. | |
| 2017/0281024 A1 | 10/2017 | Narasimhan et al. | |
| 2018/0085012 A1 | 3/2018 | Wei et al. | |
| 2018/0199824 A1 | 7/2018 | Centen et al. | |
| 2018/0289288 A1 | 10/2018 | Kim et al. | |
| 2019/0082972 A1 | 3/2019 | Tao et al. | |
| 2019/0274552 A1 | 9/2019 | Jang et al. | |

FOREIGN PATENT DOCUMENTS

| | | |
|---|---|---|
| KR | 10-2019-0107430 A | 9/2019 |
| WO | 2017/156084 A2 | 9/2017 |

OTHER PUBLICATIONS

Kim et al., "Ballistocardiogram: Mechanism and Potential for Unobtrusive Cardiovascular Health Monitoring," Scientific Reports, vol. 6, Article No. 31297, Aug. 9, 2016, pp. 1-6, 6 pages total.

Yousefian et al., "Physiological Association between Limb Ballistocardiogram and Arterial Blood Pressure Waveforms: A Mathematical Model-Based Analysis," Scientific Reports, vol. 9, Article No. 5146, Mar. 26, 2019, pp. 1-13, 13 pages total.

* cited by examiner

APPARATUS AND METHOD FOR ESTIMATING BLOOD PRESSURE

CROSS-REFERENCE TO RELATED APPLICATION(S)

This application claims priority from Korean Patent Application No. 10-2018-0167746, filed on Dec. 21, 2018, in the Korean Intellectual Property Office, the disclosure of which is incorporated herein by reference in its entirety.

BACKGROUND

1. Field

Apparatuses and methods consistent with example embodiments relate to cufflessly estimating blood pressure.

2. Description of the Related Art

As society is rapidly aging, social problems such as healthcare costs and the like are increasing. As a result, there is great interest in healthcare technology. Accordingly, not only medical devices for use in hospitals or medical examination institutions, but also small medical devices that individuals can carry are being developed. Furthermore, such small medical devices are provided in the form of wearable devices, which may be worn by users, to measure cardiovascular health states such as blood pressure and the like, thereby enabling the users to directly measure and manage cardiovascular health states.

Therefore, extensive research has been conducted recently on methods to estimate blood pressure by analyzing bio-signals, so as to manufacture the devices in a compact size while improving accuracy in estimating blood pressure.

SUMMARY

According to an aspect of an example embodiment, there is provided an apparatus for estimating blood pressure, the apparatus including: a ballistocardiogram (BCG) sensor configured to measure a limb BCG signal from a user; and a processor configured to obtain blood pressure-related features from the measured limb BCG signal, according to sensing characteristics of the BCG sensor, and estimate a blood pressure of the user based on the obtained blood pressure-related features.

The sensing characteristics of the BCG sensor may include at least one of a type and a measurement position of the BCG sensor.

The processor may include a model calibrator configured to calibrate a reference limb BCG prediction model based on the limb BCG signal measured from the user, so as to generate a personalized limb BCG prediction model according to the sensing characteristics of the BCG sensor.

The model calibrator may be further configured to select at least one parameter from among a plurality of parameters of the reference limb BCG prediction model, and generate the personalized limb BCG prediction model by adjusting the selected at least parameter based on the measured limb BCG signal.

Based on the sensing characteristics of the BCG sensor indicating that the BCG sensor is an acceleration sensor worn on a wrist of the user, the model calibrator may be configured to select at least one of mass, elasticity, and attenuation as the at least one parameter.

The processor may include a characteristic point extractor configured to convert the measured limb BCG signal by using the personalized limb BCG prediction model, and extract characteristic points based on the converted limb BCG signal.

The characteristic point extractor may be further configured to extract the characteristic points by performing beat gating on the converted limb BCG signal or based on a bio-signal measured by another sensor.

The characteristic point extractor may be further configured to extract a representative signal from the converted limb BCG signal by performing the beat gating, and extract the characteristic points from the extracted representative signal.

The processor may include a feature obtainer configured to obtain the blood pressure-related features from the extracted characteristic points according to the sensing characteristics of the BCG sensor and a correlation between a whole-body BCG signal and the limb BCG signal.

Based on the sensing characteristics of the BCG sensor indicating that the BCG sensor is an acceleration sensor worn on a wrist of the user, the feature obtainer may be further configured to obtain a J-K interval as a feature related to a pulse transit time (PTT), a K-wave amplitude as a feature related to aortic pulse pressure (PP), and a K-L amplitude as a feature related to a distal pulse pressure (PP).

The processor may include a blood pressure estimator configured to estimate the blood pressure based on the obtained blood pressure-related features by using at least one of a linear or nonlinear regression analysis model, a neural network model, and a deep learning model.

The processor may include a blood pressure estimator configured to estimate a blood pressure variation based on the obtained blood pressure-related features, and estimate the blood pressure based on the estimated blood pressure variation and a reference blood pressure measured at a calibration time by an external blood pressure measuring device.

According to an aspect of another example embodiment, there is provided a method of estimating blood pressure, the method including: measuring a limb ballistocardiogram (BCG) signal from a user, by a BCG sensor; obtaining blood pressure-related features from the limb BCG signal, based on sensing characteristics of the BCG sensor; and estimating a blood pressure of the user based on the blood pressure-related features.

The method may further include calibrating a reference limb BCG prediction model based on the limb BCG signal measured from the user, so as to generate a personalized limb BCG prediction model according to the sensing characteristics of the BCG sensor.

The generating the personalized limb BCG prediction model may include selecting at least one parameter from among a plurality of parameters of the reference limb BCG prediction model, and generating the personalized limb BCG prediction model by adjusting the selected at least one parameter based on the measured limb BCG signal.

The method may further include converting the measured limb BCG signal by using the personalized limb BCG prediction model, and extracting characteristic points based on the converted limb BCG signal.

The extracting the characteristic points may include extracting the characteristic points by performing beat gating on the converted limb BCG signal or on a bio-signal measured by another sensor.

The extracting the characteristic points may include extracting a representative signal from the converted limb BCG signal by performing the beat gating, and extracting the characteristic points from the extracted representative signal.

The obtaining the blood pressure-related features may include obtaining the blood pressure-related features from the extracted characteristic points according to the sensing characteristics of the BCG sensor and a correlation between a whole-body BCG signal and the limb BCG signal.

The obtaining the blood pressure-related features may include, based on the sensing characteristics of the BCG sensor indicating that the BCG sensor is an acceleration sensor worn on a wrist of the user, obtaining a J-K interval as a feature related to a pulse transit time (PTT), a K-wave amplitude as a feature related to aortic pulse pressure (PP), and a K-L amplitude as a feature related to distal pulse pressure (PP).

The estimating the blood pressure may include estimating the blood pressure based on the obtained blood pressure-related features by using at least one of a linear or nonlinear regression analysis model, a neural network model, and a deep learning model.

The apparatus may further include: a pulse wave sensor configured to measure a pulse wave signal from the user, wherein the processor may be further configured to estimate the blood pressure of the user based on the obtained blood pressure-related features and the pulse wave signal.

The processor may include a characteristic point extractor configured to convert the measured limb BCG signal by using a personalized limb BCG prediction model, extract characteristic points from the converted limb BCG signal by performing beat gating on the measured pulse wave signal.

The processor may include: a PTT obtainer configured to obtain a pulse transit time (PTT) based on a time interval between a predetermined characteristic point of the pulse wave signal and a predetermined characteristic point extracted from the limb BCG signal; and a blood pressure estimator configured to estimate the blood pressure based on the obtained PTT and the obtained blood pressure-related features.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
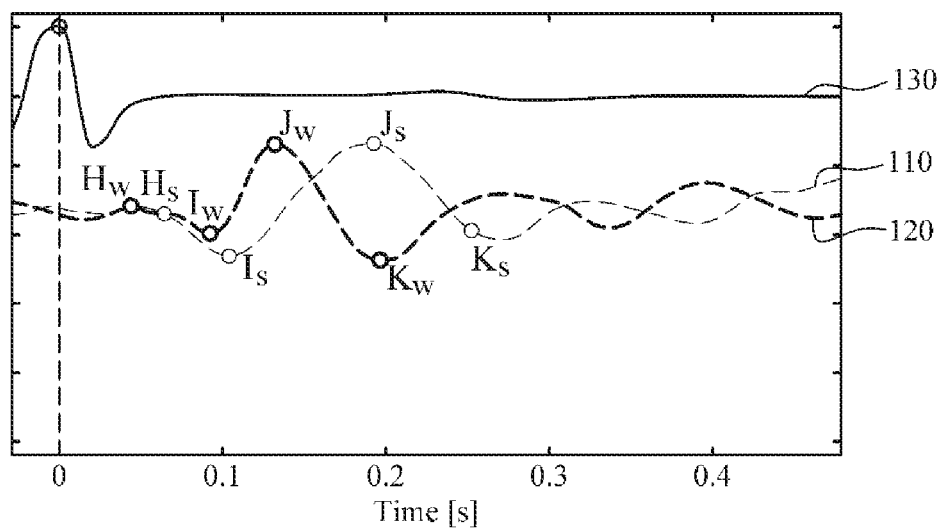
FIG. 1 is a diagram illustrating an example of a whole-body ballistocardiogram (BCG) signal and a limb BCG signal.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module,' etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, example embodiments of an apparatus and method for estimating blood pressure will be described in detail with reference to the accompanying drawings. In the embodiments which will be described below, a ballistocardiogram (BCG) signal is obtained to measure ballistic forces on the heart, and repetitive motions of the human body arising from the ejection of blood into blood vessels with each heart beat. A whole-body ballistocardiogram (BCG) signal indicates a vibration signal of the whole body which is derived from the heartbeat, and a limb BCG signal indicates a vibration signal of a limb (e.g., wrist, ankle, neck, forearm, etc.) which is derived from the heartbeat.

FIG. 1 is a diagram illustrating an example of a whole-body ballistocardiogram (BCG) signal and a limb BCG signal. The limb BCG signal 120 may be a wrist skin vibration signal measured from the wrist.

Referring to FIG. 1, it can be seen that while the whole-body BCG signal 110 and the limb BCG signal 120 have similar waveform shapes, the whole-body BCG signal 110 and the limb BCG signal 120 show different characteristics due to channel characteristics (e.g., compliant human body, etc.) and the like.

The BCG signals 110 and 120 reflect a series of mechanical movements of the body in response to cardiac ejection and blood movement through the peripheral vasculature. Primary movements are indicated by a H-peak, an I-peak, a J-peak, and a K-peak.

For example, as illustrated in FIG. 1, it can be seen that when beat gating is performed on the whole-body BCG signal 110 and the limb BCG signal 120 with respect to an R wave of an electrocardiogram (ECG) signal 130, characteristic points (e.g., Hw, Iw, Jw, and Kw) of the limb BCG signal 120 appear faster than characteristic points (e.g., Hs, Is, Js, and Ks) of the whole-body BCG signal 120; and the time difference between corresponding characteristic points is increased further toward the end of the signals.

As described above, the shape of the BCG signal varies according to sensing characteristics (e.g., types or measurement positions of the BCG sensor and the like) for measuring the BCG signal. That is, it can be seen that in the case of estimating blood pressure using the limb BCG signals which are measured by various types of limb BCG sensors attached at various positions of a user's limbs, it is difficult to apply the same criteria, applied to blood pressure-related features (e.g., I-J interval, J-K amplitude, etc.) derived from the whole-body BCG signal, equally to the limb BCG signal. Hereinafter, a description will be given of various embodiments for estimating blood pressure more accurately by redefining cardiovascular features, defined for the whole-body BCG signal, according to the sensing characteristics of the limb BCG signal.

Figure 2:
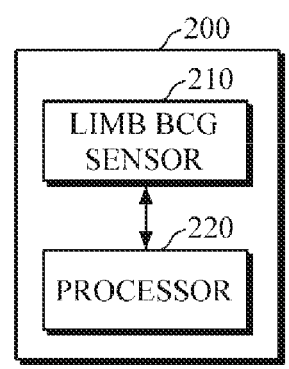
FIG. 2 is a block diagram illustrating an apparatus for estimating blood pressure according to an example embodiment.

FIG. 2 is a block diagram illustrating an apparatus for estimating blood pressure according to an example embodiment.

The blood pressure estimating apparatus 200 of FIG. 2 may be implemented as a software module or may be manufactured in the form of a hardware chip to be embedded in an electronic apparatus. In this case, examples of the electronic apparatus may include a cellular phone, a smart-phone, a tablet PC, a laptop computer, a personal digital assistant (PDA), a portable multimedia player (PMP), a navigation, an MP3 player, a digital camera, a wearable device, and the like; and examples of a wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 2, the blood pressure estimating apparatus 200 includes a limb BCG sensor 210 and a processor 220.

The limb BCG sensor 210 may be attached to a user's limbs to measure limb BCG signals. In this case, the limbs may include the wrist, the ankle, the neck, the forearm, and the like. The limb BCG sensor 210 may be attached to at least one of the limbs to measure one or more limb BCG signals. The limb BCG sensor 210 may include various types of sensors, such as an electrocardiogram (ECG) sensor, a photoplethysmography (PPG), a displacement sensor, a velocity sensor, an acceleration sensor, a load cell sensor, a polyvinylidene fluoride (PVDF) film sensor, an electromechanical film (EMFi) sensor, and the like, but is not limited thereto.

The processor 220 may control the overall operation of the blood pressure estimating apparatus 200. At predetermined intervals or in response to occurrence of a specific event such as a user command and the like, the processor 220 may drive the limb BCG sensor 210 to measure a user's BCG signals.

The processor 220 may obtain features related to blood pressure (hereinafter referred to as blood pressure-related features) by analyzing the limb BCG signal measured by the limb BCG sensor 210, and may estimate a user's blood pressure based on all or some of the obtained blood pressure-related features. The processor 220 may obtain the blood pressure-related features by considering sensing characteristics such as the types or measurement positions of the limb BCG sensor 210 attached to the user. For example, the processor 220 may obtain the blood pressure-related features according to sensing characteristics of the limb BCG sensor 210 attached to the user by using a limb BCG prediction model which defines a correlation between the whole-body BCG signal and the limb BCG signal.

The following description will be given of various embodiments for estimating blood pressure, but the is not limited thereto, and the processor 220 may measure or evaluate various cardiovascular features, such as arterial stiffness, cardiac output, stroke volume, and the like, other than blood pressure, by analyzing the limb BCG signal.

Hereinafter, the processor 220 will be described in further detail with reference to FIGS. 3, 4A, and 4B.

Figure 3:
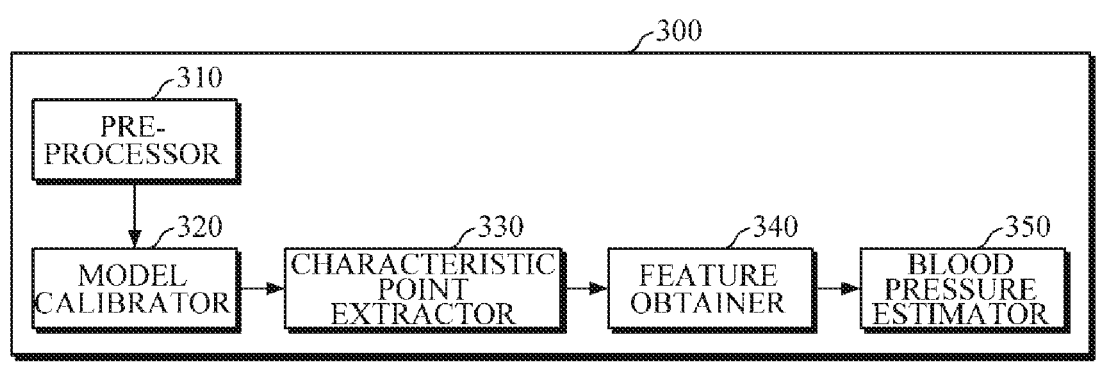
FIG. 3 is a block diagram illustrating an example of a processor of FIG. 2.
Figure 4A:
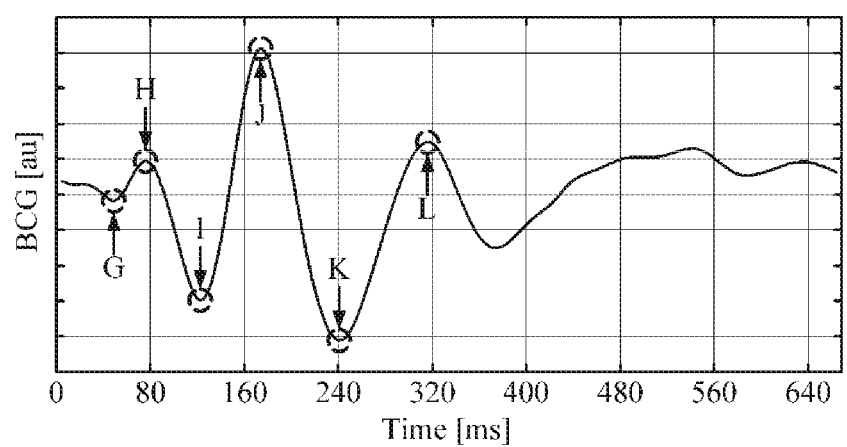
FIGS. 4A and 4B are diagrams explaining an example of estimating blood pressure using a limb BCG signal.
Figure 4B:
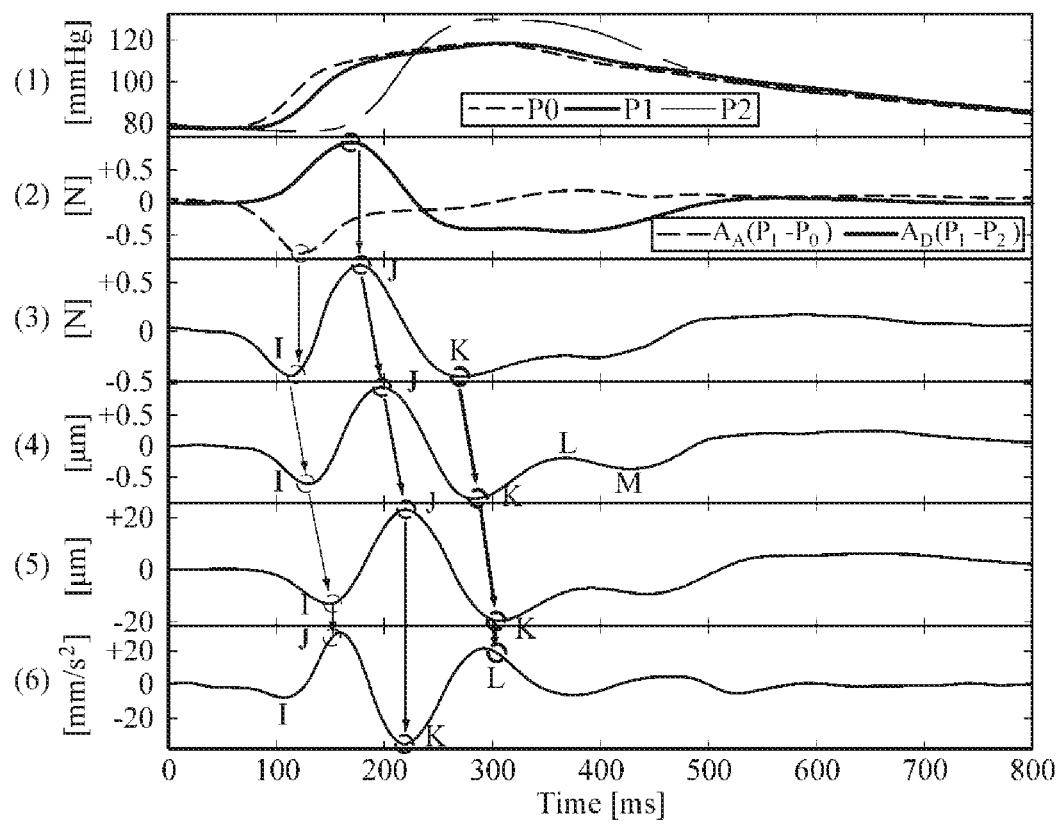

FIG. 3 is a block diagram illustrating an example of a processor of FIG. 2; and FIGS. 4A and 4B are diagrams explaining an example of estimating blood pressure using a limb BCG signal.

Referring to FIG. 3, the processor 300 includes a preprocessor 310, a model calibrator 320, a characteristic point extractor 330, a feature obtainer 340, and a blood pressure estimator 350.

Upon receiving a limb BCG signal from the limb BCG sensor 210, the preprocessor 310 may remove noise from the limb BCG signal by using various noise removal methods such as filtering, smoothing, and the like. For example, the preprocessor 310 may perform band-pass filtering between 0.5 Hz to 15 Hz, or may perform equalization, such as exponential moving average and the like, for multiple limb movement beats.

Once the limb BCG signal is measured from a user's limb, the model calibrator 320 may calibrate a reference limb BCG prediction model based on the measured limb BCG signal, to generate a limb prediction model personalized for the user. In this case, the reference limb BCG prediction model is a prediction model which defines a correlation between the whole-body BCG signal and the limb BCG signal, and may be predefined through various experiments. The reference limb BCG prediction model may be a model which is reduced to a four degree-of-freedom (DOF) vibrational transmission model for four body parts associated with the limbs (e.g., upper body, lower body, arm-wrist-hand, and internal organs) by using a human body model based on a lumped parameter, for example, a 16 degree-of-freedom (DOF) model for the whole body.

For example, once the limb BCG signal for calibration is measured from the user's limb, the model calibrator 320 may select at least some parameters from among a plurality of parameters of the reference limb BCG prediction model, and may generate the limb BCG prediction model, personalized for the user, by adjusting the selected parameter values based on the measured limb BCG signal. As will be described later, the BCG prediction model personalized for the user may be used to eliminate the effect of channel characteristics, among factors that affect estimation of blood pressure, from the user's limb BCG signal for estimating blood pressure.

In addition, the model calibrator 320 may select a parameter which is sensitively affected by each of the sensing characteristics of the limb BCG sensor 210 which measures the limb BCG signal. For example, in the case in which a measurement position for sensing characteristics of the limb BCG sensor 210 is a user's wrist, and the type of the limb BCG sensor 210 is an acceleration sensor, the model calibrator 320 may select parameters, such as mass of the arm, stiffness of the upper body, an arm damper, and the like, as parameters which are sensitively affected by the sensing characteristics of the limb BCG sensor 210. Further, in the case in which the limb BCG sensor 210 is a scale sensor, the model calibrator 320 may select parameters, such as mass of the arm, stiffness of the upper body, a leg damper, and the like, as parameters which are sensitively affected by the sensing characteristics of the limb BCG sensor 210. However, the parameters are not limited thereto, and the model calibrator 320 may select various other parameters by considering user characteristics (e.g., a user's health condition, age, sex, etc.) alone or in combination with the sensing characteristics of the limb BCG sensor 210.

The model calibrator 320 may determine whether to perform model calibration by analyzing a blood pressure estimation result, and may perform model calibration based on the analysis. Alternatively, in response to a user's request, or upon determining that sensing characteristics of the limb BCG sensor 210 are changed, the model calibration 320 may perform model calibration.

Once the limb BCG sensor 210 measures the limb BCG signal for estimating blood pressure, the characteristic point extractor 330 may convert the measured limb BCG signal based on the personalized limb BCG prediction model, to obtain the converted limb BCG signal, from which the effect of the sensing characteristics of the limb BCG sensor 210 is eliminated.

The characteristic point extractor 330 may extract characteristic points based on the converted limb BCG signal. FIG. 4A illustrates an example of a converted limb BCG signal, which is obtained by converting the limb BCG signal measured by an acceleration sensor from a user's wrist. As illustrated in FIG. 4A, the converted limb BCG signal is basically based on a reference limb BCG prediction model which defines a correlation between the whole-body BCG signal and the limb BCG signal, such that the characteristic point extractor 330 may extract characteristic points G, H, I, J, K, L related to blood pressure, and the like, which are similar to those of the whole-body BCG signal, from the converted limb BCG signal. A G wave may refer to a small footward wave which at times precedes an H wave. An H wave may indicates headward deflection that begins close to the peak of an R-wave, maximum peak sychronously or near the start of ejection. An I wave may indicate footward deflection that follows the H-wave. A J wave may be the largest headward wave that immediately follows the I-wave. A K wave may be a footward wave following the J wave and may occur before the end of systole. A L wave indicates a small headward deflection that follows the K wave. The F and G waves may belong to a pre-systolic group. The H, I, J, and K waves may be considered as systolic waves. The L wave may be considered as a diastolic wave.

In order to extract such characteristic points, the characteristic point extractor 330 may perform beat gating by using a specific characteristic point, e.g., J-peak, of the converted signal, or by using a bio-signal, such as electrocardiography (ECG) or photoplethysmography (PPG), which is measured by other sensors. The term "beat gating" may refer to extracting one cycle of an BCG interval from a continuously measured BCG signal.

Further, the characteristic point extractor 330 may divide the converted signal in an analysis interval into periods to obtain a plurality of one-period signals, and may extract characteristic points from each of the plurality of one-period signals and combine the extracted characteristic points, or may determine a representative signal from among the plurality of one-period signals and extract characteristic points from the determined representative signal.

For example, the characteristic point extractor 330 may analyze the shape of the converted limb BCG signal itself, to divide the signal into periods. Alternatively, the characteristic point extractor 330 may also divide the signal into periods by performing beat gating based on a specific point (e.g., start point, peak point, etc.) of other bio-signals (e.g., ECG signal, PPG signal, etc.) which are measured along with the limb BCG signal.

The characteristic point extractor 330 may determine any one of the plurality of one-period signals as a representative signal according to predetermined criteria. For example, the characteristic point extractor 330 may determine, as a representative waveform, a one-period signal appearing first or a one-period signal having the highest J-peak among the plurality of one-period signals. In another example, the characteristic point extractor 330 may determine a representative signal based on similarity between the plurality of one-period signals. For example, the characteristic point extractor 330 may determine, as a representative signal, any one of the one-period signals which has the highest average value of similarities with other one-period signals among the plurality of one-period signals. In addition, the characteristic point extractor 330 may determine, as a representative signal, an ensemble average of a predetermined number of one-period signals having a high average value of similarities with other one-period signals among the plurality of one-period signals; or may determine, as a representative signal, an ensemble average of two or more one-period signals having an average value of similarities with other one-period signals, which is greater than or equal to a predetermined threshold value, among the plurality of one-period signals.

In this case, various similarity calculation algorithms may be used, including Euclidean distance, Manhattan Distance, Cosine Distance, Mahalanobis Distance, Jaccard Coefficient, Extended Jaccard Coefficient, Pearson's Correlation Coefficient, Spearman's Correlation Coefficient, and the like.

The feature obtainer 340 may obtain blood pressure-related features by using the extracted characteristic points. In this case, the feature obtainer 340 may obtain the blood pressure-related features according to the sensing characteristics of the limb BCG sensor 210 by considering a correlation between the whole-body BCG signal and the limb BCG signal.

FIG. 4B is a diagram illustrating a correlation between a whole-body BCG signal and a limb BCG signal measured from a wrist. Referring to FIG. 4B, (1) illustrates aortic pressure, in which P0 denotes blood pressure at the inlet of the ascending aorta; P1 denotes blood pressure at the outlet of the ascending aorta or at the inlet of the descending aorta; and P2 denotes blood pressure at the outlet of the descending aorta. Further, (2) illustrates signals obtained by adjusting the aortic pressure, in which AA denotes a BP gradient in the ascending aorta; and AD denotes a BP gradient in the descending aorta.

In addition, (3) illustrates a whole-body BCG signal. As illustrated therein, characteristic points I, J, K, and the like of the whole-body BCG signal are related to the aortic pressure. Generally, it is known that an I-J interval of the whole-body BCG signal is related to a pulse transit time (PTT), and a J-wave amplitude is related to aortic pulse pressure (PP), and a J-K amplitude is related to distal pulse pressure. Accordingly, blood pressure may be estimated using these blood pressure-related features.

Further, (4) illustrates a BCG signal obtained by measuring displacement from a user's leg using a scale; (5) illustrates a limb BCG signal obtained by measuring displacement from a user's wrist; and (6) illustrates a limb BCG signal obtained by measuring acceleration from the wrist.

Referring to FIG. 4B, it can be seen that blood pressure-related characteristic points I, J, and K of the whole-body BCG signal 3 are mapped correspondingly to the characteristic points I, J, and K of the BCG signals 4 and 5 obtained by measuring displacement from the wrist, the leg, and the like. However, the characteristic points J, K, and L of the BCG signal 6 obtained by measuring acceleration of the wrist are mapped to the characteristic points I, J, and K of the whole-body BCG signal 3.

In other words, it is required to re-define blood pressure-related features of the whole-body BCG signal, which are used for estimating blood pressure, according to sensing characteristics of the limb BCG sensor to correspond to the limb BCG signal. The following Table 1 shows a correlation between blood pressure-related features of the whole-body BCG signal and blood pressure-related features of the limb BCG signal obtained using a wrist acceleration sensor. However, this is merely an example, and the blood pressure-related features may also be defined differently according to sensing characteristics of the limb BCG sensor and/or user characteristics.

TABLE 1

| Physiological meaning | Whole-body BCG signal | Limb BCG signal obtained using wrist acceleration sensor |
|---|---|---|
| Arterial stiffness Pulse transit time (PTT) | I-J interval | J-K interval |
| Aortic pulse pressure (PP) | J amplitude | K amplitude |
| Distal pulse pressure (PP) | J-K amplitude | K-L amplitude |

The feature obtainer 340 may combine one or more characteristic points extracted from the converted limb BCG signal, and may obtain features, re-defined according to the sensing characteristics of the limb BCG sensor, as blood pressure-related features. For example, in the case in which a sensing characteristic of the limb BCG sensor 210 attached to a user is an acceleration sensor worn on the wrist, the feature obtainer 340 may obtain a J-K time interval as a feature related to pulse transit time or arterial stiffness, may obtain a K amplitude as a feature related to aortic PP, and may obtain a K-L amplitude as a feature related to distal PP. The J-K time interval may correspond to an I-J interval of a force BCG and is associated with aortic PTT. However, the features are not limited thereto, and may obtain a time and an amplitude of each characteristic point, a time interval or an amplitude interval between two different characteristic points, a ratio between the obtained values, and the like as blood pressure-related features.

The blood pressure estimator 350 may estimate blood pressure by using the blood pressure-related features obtained by the feature obtainer 340. For example, upon obtaining information including the J-K interval, the K-wave amplitude, the K-L amplitude, and the like which are related to pulse transit time, vascular compliance, pulse pressure, and the like, the blood pressure estimator 350 may estimate blood pressure by applying a blood pressure estimation model to the obtained blood pressure-related features. The K-wave amplitude may refer to a peak point value of the K wave, and the K-L amplitude may refer to the amplitude between the peak point value of the K wave and a peak point value of the L wave. In this case, the blood pressure estimation model may be pre-defined using various methods such as linear/nonlinear regression analysis, neural network, deep learning, and the like. The blood pressure estimation model may be defined for mean arterial pressure, systolic blood pressure, and diastolic blood pressure.

In addition, the blood pressure estimation model may be a model for estimating mean arterial pressure. For example, the following Equation 1 defines a relationship between vascular compliance-related features (e.g., pulse transit time, pulse wave velocity, etc.) and mean arterial pressure, and is one of various known types of equations. The following Equation 2 is an equation which defines a relationship between mean arterial pressure and pulse pressure. However, Equations 1 and 2 are merely examples, and the blood pressure estimation model is not limited thereto and may be modified in various forms or may be newly defined.

$$PWV = \frac{\text{distance}}{PTT} = \sqrt{\frac{Eh}{2\rho r}} \quad \text{[Equation 1]}$$

$$E = E_0 e^{\alpha MAP}$$

$$PWV = \frac{\text{distance}}{PTT} = \sqrt{\frac{E_0 e^{\alpha MAP} h}{2\rho r}}$$

$$\alpha \log PWV + \beta = MAP$$

Herein, the first equation is the Moens-Korteweg equation, and the second equation is the Hughes equation, in which E denotes the vascular compliance, h denotes the thickness of blood vessel walls, r denotes the radius of blood vessels, ρ denotes the density of blood, and P denotes blood pressure.

$$MAP = DBP + \tfrac{1}{3}(SBP - DBP)$$

$$PP = SBP - DBP \quad \text{[Equation 2]}$$

Upon obtaining features related to the pulse transit time or the vascular compliance and features (e.g., K-L amplitude) related to pulse pressure from the limb BCG signal, the blood pressure estimator 350 may first estimate mean arterial pressure by using the blood pressure estimation model such as the above Equation 1, and may estimate systolic blood pressure/diastolic blood pressure by combining the mean arterial pressure, estimated by the above Equation 2, with the features related to pulse pressure.

In addition, the blood pressure estimator 350 may estimate a blood pressure variation compared to a calibration time by using the blood pressure-related features and the blood pressure estimation model. Upon estimating the blood pressure variation, the blood pressure estimator 350 may estimate blood pressure by correcting an offset by using a reference blood pressure value measured at the calibration time by an external device such as a cuff-type blood pressure measuring device.

Figure 5:
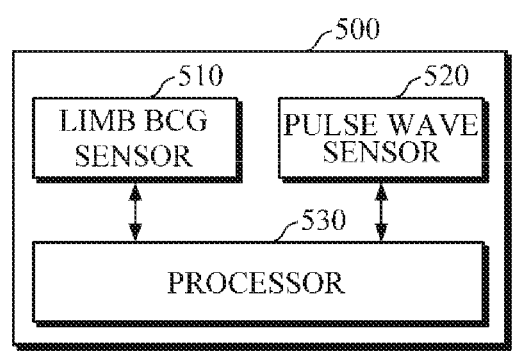
FIG. 5 is a block diagram illustrating an apparatus for estimating blood pressure according to an example embodiment.
Figure 6:
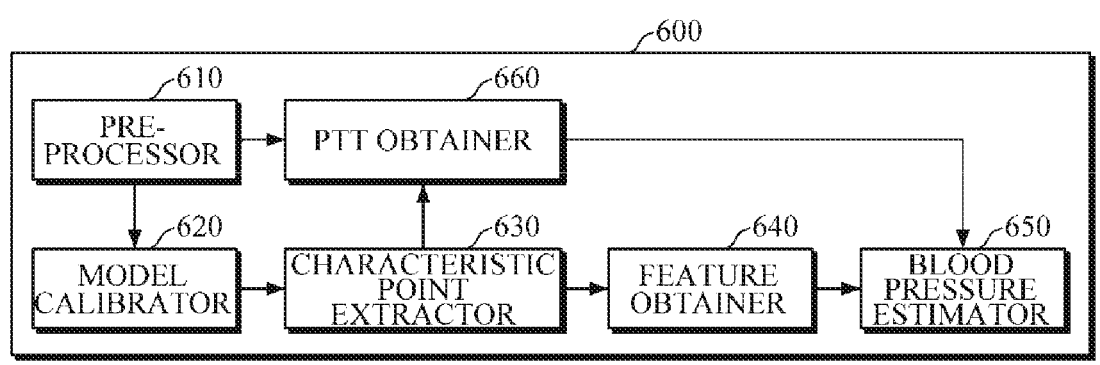
FIG. 6 is a block diagram illustrating an example of a processor of FIG. 5.

FIG. 5 is a block diagram illustrating an apparatus for estimating blood pressure according to an example embodiment. FIG. 6 is a block diagram illustrating an example of a processor 530 of FIG. 5.

Referring to FIG. 5, the blood pressure estimating apparatus 500 includes a limb BCG sensor 510, a pulse wave sensor 520, and a processor 530. The limb BCG sensor 510 and the processor 530 are described above, such that detailed description thereof will be omitted.

The limb BCG sensor 510 may measure limb BCG signals from a user's limbs under the control of the processor 530.

The pulse wave sensor 520 may measure pulse wave signals, including a PPG signal, from the user. The pulse wave sensor 520 may include a light source which emits light onto skin of the user, and a detector which detects scattered or reflected light when light emitted by the light source is scattered or reflected from the skin of the user. The light source may include a light emitting diode (LED), a laser diode, a fluorescent body, and the like, and may be formed as one or two or more arrays. Further, the light source may emit light of different wavelengths. The detector may include a photodiode, an image sensor, and the like, and may be formed as one or two or more arrays.

In response to occurrent of an event of estimating blood pressure, the processor 520 may control the limb BCG sensor 510 and the pulse wave sensor 520. The event of estimating blood pressure may be generated in response to a user's request or may be generated automatically at predetermined intervals for continuous estimation of blood pressure.

The processor 530 may receive the limb BCG signal and the pulse wave signal from the limb BCG sensor 510 and the pulse wave sensor 520 respectively, and may estimate blood pressure by using the received limb BCG signal and pulse wave signal.

Referring to FIG. 6, a processor 600 includes a preprocessor 610, the model calibrator 620, a characteristic point extractor 630, a feature obtainer 640, a blood pressure estimator 650, and a PTT obtainer 660. The preprocessor 610, the model calibrator 620, the characteristic point extractor 630, the feature obtainer 640, and the blood pressure estimator 650 are described above in detail, such that a description thereof will be briefly given below.

The preprocessor 610 may receive the limb BCG signal and/or the pulse wave signal, and may remove noise and the like by preprocessing the received BCG signal and/or pulse wave signal. The preprocessor 610 may perform preprocessing, such as band-pass filtering, smoothing, equalization of beats of continuously measured signals, and the like.

Once the limb BCG signal is measured for calibration, the model calibrator 620 may generate the limb BCG prediction model personalized for a user by calibrating the reference limb BCG prediction model, which defines a correlation between the whole-body BCG signal and the limb BCG signal, based on the measured limb BCG signal as described above.

The characteristic point extractor 630 may convert the measured limb BCG signal based on the personalized limb BCG prediction model, and may extract characteristic points by using the converted limb BCG signal. In this case, the characteristic point extractor 630 may extract a representative signal from the converted limb BCG signal in a unit interval, and may extract characteristic points from the extracted representative signal. Further, the characteristic point extractor 630 may extract a representative signal and characteristic points by performing beat gating based on a start point or other characteristic point, e.g., a peak point, of the pulse wave signal measured by the pulse wave sensor 520. However, the characteristic point extractor 630 is not limited thereto, and may perform beat gating based on any characteristic point (e.g., J-peak) of the converted BCG signal or based on other bio-signal if any other bio-signal is measured.

The feature obtainer 640 may obtain various blood pressure-related features from the converted limb BCG signal by considering a correlation between the whole-body BCG signal and the limb BCG signal. For example, in the case in which a sensing characteristic of the limb BCG sensor 510 is an acceleration sensor worn on the wrist, the feature obtainer 640 may obtain, from the limb BCG signal, the J-K interval, the K-L amplitude, the K amplitude, and the like as features each corresponding to the interval, the J-K amplitude, the amplitude, and the like which are blood pressure-related features of the whole-body BCG signal.

The PTT obtainer 660 may calculate a pulse transit time (PTT) by using the converted limb BCG signal and the pulse wave sinal. For example, the PTT obtainer 60 may calculate the PTT by calculating a time interval between any characteristic point (e.g., start point, peak point, etc.) of the pulse wave signal and any characteristic point (e.g., J-peak) of the converted limb BCG signal.

The blood pressure estimator 650 may estimate blood pressure based on the blood pressure-related features and the PTT by applying a blood pressure estimation model. In this case, the blood pressure estimation model may be predefined using various methods such as linear/nonlinear regression analysis, neural network, deep learning, and the like. The blood pressure estimation model may be defined for each of mean arterial pressure, systolic blood pressure, and diastolic blood press such that the blood pressure estimator 650 may independently estimate mean arterial pressure, systolic blood pressure, and diastolic blood pressure. Alternatively, the blood pressure estimation model may be a model for estimating mean arterial pressure based on the PTT as represented by the above Equation 1, in which case upon estimating mean arterial pressure, the blood pressure estimator 650 may estimate systolic blood pressure/diastolic blood pressure by combining mean arterial pressure with features related to pulse pressure. The blood pressure estimator 650 may estimation a blood pressure variation compared to a calibration time by using the blood pressure estimation model, and may obtain an estimated blood pressure value by correcting an offset by using a reference blood pressure value measured at the calibration time by an external device such as a cuff-type blood pressure measuring device.

Figure 7:
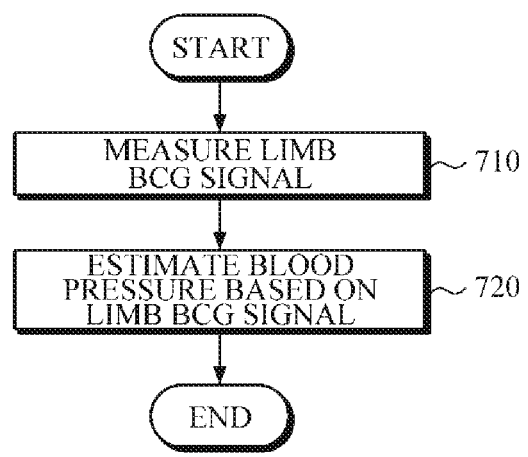
FIG. 7 is a flowchart illustrating a method of estimating blood pressure according to an example embodiment.

FIG. 7 is a flowchart illustrating a method of estimating blood pressure according to an example embodiment. The blood pressure estimating method of FIG. 7 may be an example of a blood pressure estimating method performed by the blood pressure estimating apparatus 200 of FIG. 2, which is described above in detail such that a description thereof will be briefly given below.

Referring to FIG. 7, the blood pressure estimating apparatus 200 may measure a limb BCG signal using a limb BCG sensor attached to a user in operation 710.

Then, the blood pressure estimating apparatus 200 may estimate blood pressure using the limb BCG signal in operation 720. In this case, the blood pressure estimating apparatus 200 may estimate blood pressure by considering sensing characteristics of the limb BCG sensor.

Figure 8:
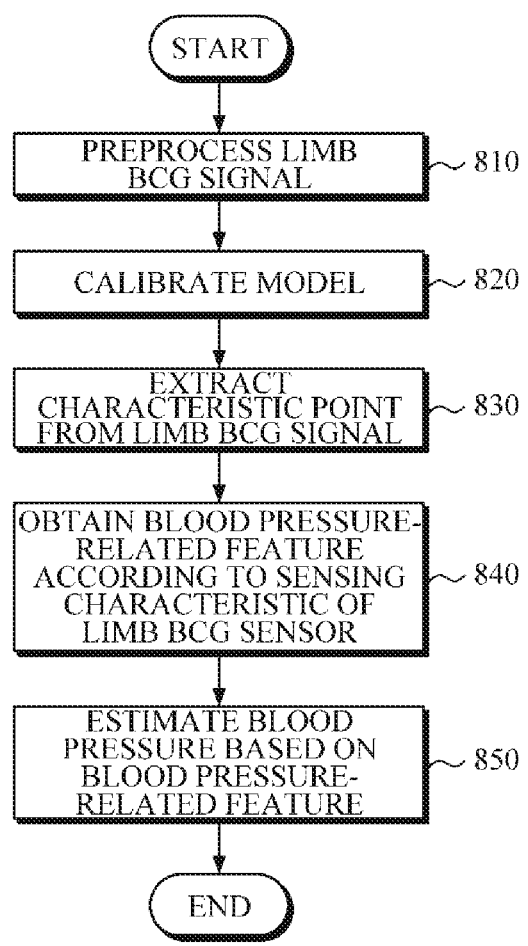
FIG. 8 is a flowchart illustrating an example of the estimating of blood pressure in operation 720.

FIG. 8 is a flowchart illustrating an example of the estimation of blood pressure in operation 720. By reference to FIG. 8, an example of estimating blood pressure using a limb BCG signal will be described below.

Upon receiving a limb BCG signal from a limb BCG sensor, the blood pressure estimating apparatus may preprocess the received limb BCG signal in operation 810. For example, the blood pressure estimating apparatus may remove noise from the limb BCG signal by using various noise removal methods such as filtering, smoothing, and the like.

Then, the blood pressure estimating apparatus may generate a personalized limb BCG prediction model by calibrating a reference limb BCG prediction model based on the limb BCG signal for calibration in operation 820. The reference limb BCG prediction model, which defines a correlation between the whole-body BCG signal and the limb BCG signal, may be a general-purpose model which may be applied to a plurality of users. Upon measuring the limb BCG signal for calibration from a user, the blood pressure estimating apparatus may generate a personalized limb BCG prediction model by adjusting at least some parameters of the reference limb BCG prediction model according to sensing characteristics of the user's limb BCG signal. The operation 820 may be performed at the calibration time, and may be omitted at the time of measurement of blood pressure.

Subsequently, the blood pressure estimating apparatus may extract characteristic points related to blood pressure from the limb BCG signal for estimating blood pressure in operation 830. For example, the blood pressure estimating apparatus may extract characteristic points (e.g., G, H, I, J, K, L, etc.) related to blood pressure by performing beat gating based on any characteristic point (J-peak) of the limb BCG signal or any characteristic point (e.g., a start point or a peak point of R-wave of electrocardiogram or pulse wave) of other bio-signal. In this case, the blood pressure estimating apparatus may convert the limb BCG signal, measured for estimating blood pressure, by using the personalized limb BCG prediction model generated in operation 820, and may extract characteristic points based on the converted limb BCG signal. Further, by performing beat gating as described above, the blood pressure estimating apparatus may obtain a plurality of one-period signals in a unit interval of the converted limb BCG signal, and may determine a representative signal from among the obtained plurality of one-period signals and extract characteristic points from the determined representative signal.

Next, the blood pressure estimating apparatus may obtain blood pressure-related features by combining one or more of the extracted characteristic points in operation 840. In this case, the blood pressure estimating apparatus may obtain, from the converted limb BCG signal, the blood pressure-related features, which correspond to blood pressure-related features of the whole-body BCG signal, according to the sensing characteristics of the limb BCG sensor by considering a correlation between the whole-body BCG signal and the limb BCG signal.

Then, the blood pressure estimating apparatus may estimate blood pressure based on the obtained blood pressure-related features in operation 850. The blood pressure estimation model may be pre-defined using various methods such as linear/nonlinear regression analysis, neural network, deep learning, and the like. Upon obtaining the blood pressure-related features, the blood pressure estimating apparatus may estimate blood pressure by applying the blood pressure estimation model to the obtained blood pressure-related features.

Figure 9:
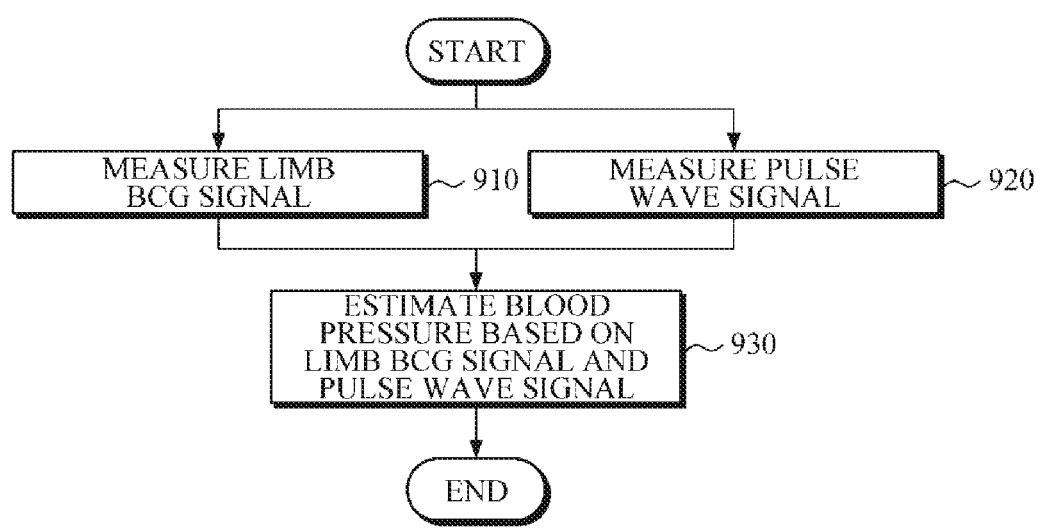
FIG. 9 is a flowchart illustrating a method of estimating blood pressure according to another example embodiment.

FIG. 9 is a flowchart illustrating a method of estimating blood pressure according to another example embodiment. The blood pressure estimating method of FIG. 9 may be an example of a blood pressure estimating method performed by the blood pressure estimating apparatus 500 of FIG. 5.

Referring to FIG. 9, the blood pressure estimating apparatus 500 may measure a limb BCG signal using a limb BCG sensor attached to a user in operation 910, and may measure a pulse wave signal using a pulse wave sensor in operation 920. The limb BCG signal and the pulse wave signal may be measured at the same time.

Then, the blood pressure estimating apparatus 500 may estimate blood pressure using the limb BCG signal and the pulse wave signal in operation 930.

Figure 10:
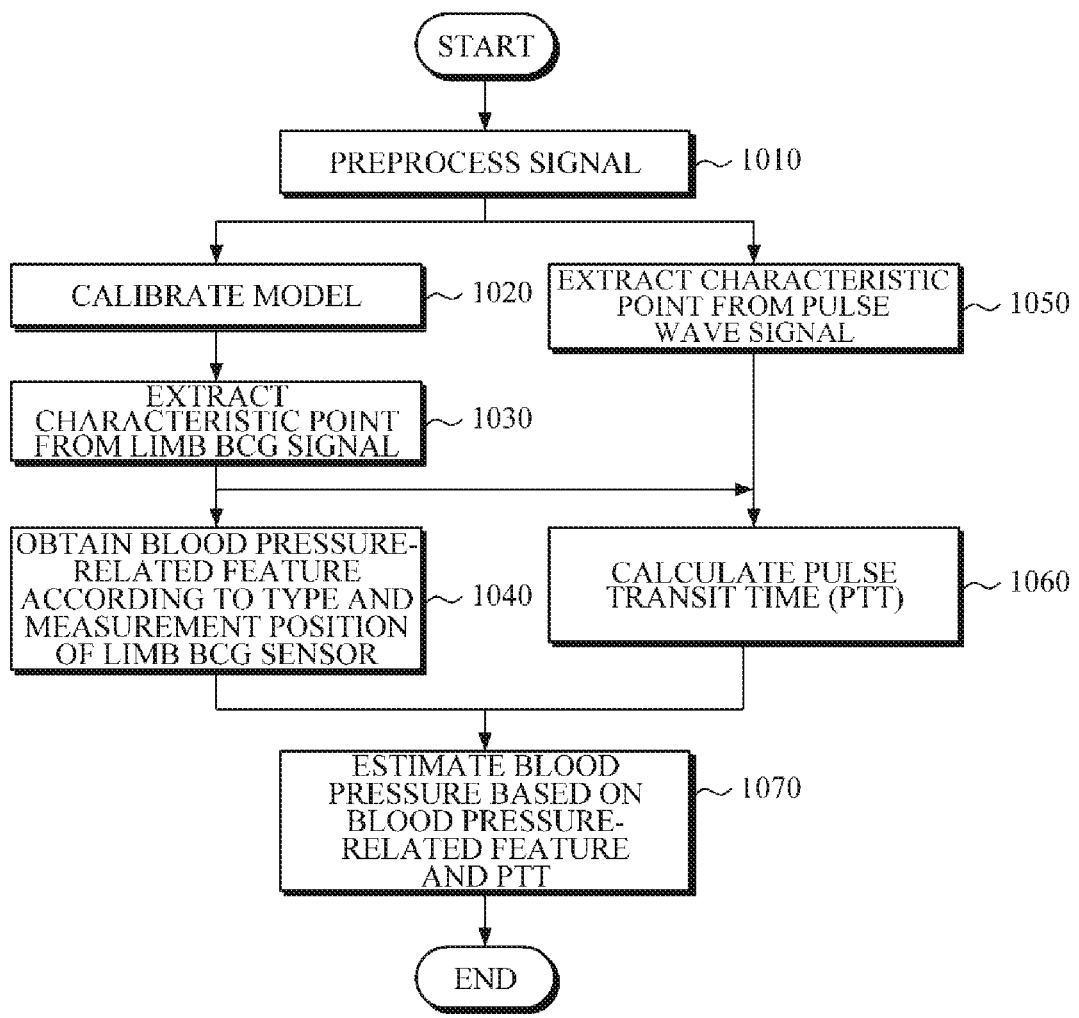
FIG. 10 is a flowchart illustrating an example of the estimating of blood pressure in operation 930.

FIG. 10 is a flowchart illustrating an example of the estimating of blood pressure in operation 930. By reference to FIG. 10, an example of estimating blood pressure using a limb BCG signal and a pulse wave signal will be described below.

Upon receiving a limb BCG signal from a limb BCG sensor and/or a pulse wave signal from a pulse wave sensor, the blood pressure estimating apparatus may preprocess the received signal in operation 1010.

Then, the blood pressure estimating apparatus may generate a personalized limb BCG prediction model by calibrating a reference limb BCG prediction model based on the limb BCG signal for calibration in operation 1020. The operation 1020 may be performed at the calibration time, and may be omitted at the time of measurement of blood pressure.

Subsequently, the blood pressure estimating apparatus may extract characteristic points related to blood pressure from the limb BCG signal for estimating blood pressure in operation 1030. For example, the blood pressure estimating apparatus may convert the limb BCG signal by using the personalized limb BCG prediction model generated in operation 1020, and may extract characteristic points related to blood pressure by performing beat gating based on any characteristic point of the converted limb BCG signal or any characteristic point of other bio-signal. Further, the blood pressure estimating apparatus may determine a representative signal from among a plurality of one-period signals in a unit interval of the converted limb BCG signal, and may extract characteristic points from the determined representative signal.

Next, the blood pressure estimating apparatus may obtain blood pressure-related features by combining one or more of the extracted characteristic points based on a correlation between the whole-body BCG signal and the limb BCG signal in operation 1040.

Upon preprocessing the pulse wave signal in operation 1010, the blood pressure estimating apparatus may extract characteristic points from the pulse wave rial in operation 1050, and may calculate a pulse transit time (PTT) in 1060 by calculating a time interval between any characteristic point (e.g., start point, peak point, etc.) extracted from the pulse wave signal and any characteristic point (e.g., J-peak) extracted from the converted BCG signal in operation 1030.

Then, the blood pressure estimating apparatus may estimate blood pressure in operation 1070 based on the blood pressure-related features obtained in 1040 and the PTT obtained operation 1060. In this case, the blood pressure estimation model for estimating blood pressure may be pre-defined based on blood pressure-related features, for example, features related to pulse pressure and the PTT.

Figure 11:
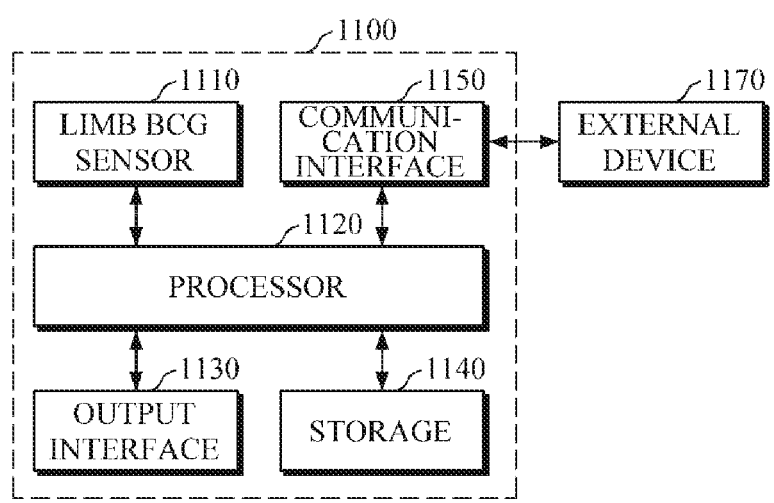
FIG. 11 is a block diagram illustrating an apparatus for estimating blood pressure according to another example embodiment.

FIG. 11 is a block diagram illustrating an apparatus for estimating blood pressure according to another example embodiment.

Referring to FIG. 11, the blood pressure estimating apparatus 1100 includes a limb BCG sensor 1110, a processor 1120, an output interface 1130, a storage 1140, and a communication interface 1150.

Here, the limb BCG sensor 1110 and the processor 1120 are described above with reference to FIGS. 2 to 6, such that a detailed description thereof will be omitted. Further, although not illustrated herein, the blood pressure estimating apparatus 1100 according to the embodiment may also include a pulse wave sensor.

The output interface 1130 may output various processing results generated and processed by the blood pressure estimating apparatus 1100. For example, the output interface 1130 may output limb BCG signals and pulse wave signals which are measured by the limb BCG sensor 1110 and the pulse wave sensor respectively. In addition, the output interface 1130 may output the limb BCG signal converted by the processor 1120, a blood pressure estimation result, and the like. In this case, the output interface 1130 may output such various data by using at least one of an acoustic method, a visual method, and a tactile method. To this end, the output interface 1130 may include a visual output module such as a display, an audio output module such as a speaker, a haptic module for providing vibrations or tactile sensation, and the like.

The storage 1140 may store programs or commands for operation of the blood pressure estimating apparatus 1100, and may store data input to and output from the blood pressure estimating apparatus 1100. For example, the storage 1140 may store reference information for driving the limb BCG sensor 1110, the pulse wave sensor, and the like. In addition, the storage 1140 may store user characteristics, sensing characteristics of a user's limb BCG sensor, a blood pressure estimation model required for estimating blood pressure, a reference limb BCG prediction model, a personalized limb BCG prediction model, and the like, as well as a blood pressure estimation result.

The storage 1140 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the storage 1140 may include an external storage medium such as web storage and the like.

The communication interface 1150 may perform communication with an external device 1170. For example, the communication interface 1150 may transmit data used by the blood pressure estimating apparatus 1100, processing result data of the blood pressure estimating apparatus 1100, and the like to the external device 1170, or may receive, from the external device 1170, various data, e.g., the reference blood pressure, the blood pressure estimation model, the reference limb BCG prediction model, and the like which are required for estimating blood pressure.

In this case, the external device 1170 may be medical equipment (e.g., cuff-type blood pressure measuring device) which uses the data used by the blood pressure estimating apparatus 1100, the processing result data of the blood pressure estimating apparatus 1100, and the like, or generates data required for estimating blood pressure, a printer to print out results, or a display to display the results. In addition, the external device 1170 may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communication interface 1150 may communicate with the external device 1170 by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WWI communication, Radio Frequency Identification (RFID) communication, 3G communication, 4G communication, 5G communication, and the like. However, this is merely exemplary and is not intended to be limiting.

Figure 12:
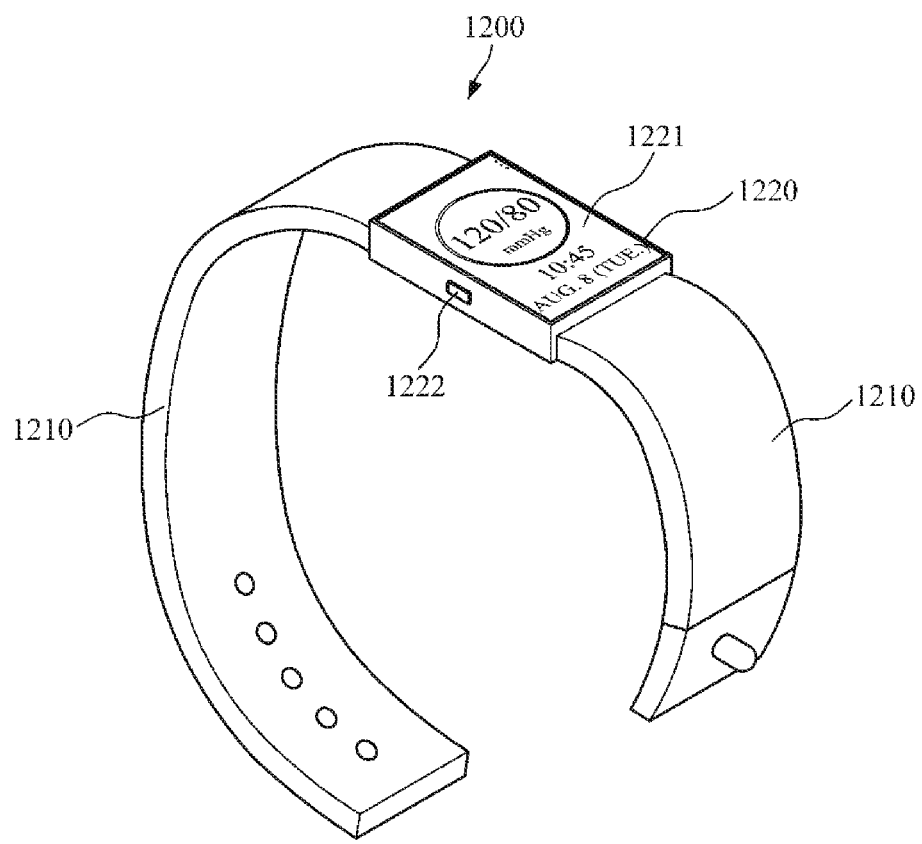
FIG. 12 is a diagram illustrating an example of a wrist-type wearable device.

FIG. 12 is a diagram illustrating an example of a wrist-type wearable device.

Referring to FIG. 12, the wrist-type wearable device 1200 includes a strap 1210 and a main body 1220.

The strap 1210 may be connected to both ends of the main body 1220 so as to be fastened in a detachable manner or may be integrally formed therewith as a smart band. The strap 1210 may be made of a flexible material to be wrapped around a user s wrist so that the main body 1220 may be worn on the wrist.

The main body 1220 may include the aforementioned blood pressure estimating apparatuses 200, 500, and 1100. Further, the main body 1220 may include an acceleration sensor for measuring BCG signals from a user's wrist. Further, a pulse wave sensor, which emits light onto the user's wrist, and detects light returning from the wrist skin, may be mounted on a rear face of the main body 1220. In addition, the main body 1220 may include a processor which is electrically connected to the acceleration sensor or the pulse wave sensor, and estimates blood pressure as described above.

A battery, which supplies power to the wrist-type wearable device 1200, may be mounted in the main body 1220.

The wrist-type wearable device 1200 may further include a display 1221 and a manipulator 1222 which are mounted at the main body 1220. The display 1221 may display data processed by the wrist-type wearable device 1200, processing result data thereof, and the like. The display 1221 may include a touch screen which allows touch input, and may receive a touch input from a user and transmit the received input to the processor.

The manipulator 1222 may receive input of various control signals from a user. The manipulator 1222 may include a power button to turn on/off the wearable device 1200.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating blood pressure, the apparatus comprising:
    a ballistocardiogram (BCG) sensor comprising an acceleration sensor configured to measure a limb BCG signal from a user; and
    a processor configured to:
        based on a sensor type and a measurement position of the BCG sensor, at a time when the limb BCG signal is measured, corresponding to the acceleration sensor and a wrist of the user, respectively, calibrate a reference limb BCG prediction model based on a parameter that is set according to mass of an arm with the wrist, to obtain a personalized limb BCG prediction model,
        convert, by using the personalized limb BCG prediction model that is personalized based on the sensor type and the measurement position of the BCG sensor at the time when the limb BCG signal is measured, the measured limb BCG signal to a converted limb BCG signal, in which a noise effect caused by the sensor type and the measurement position of the BCG sensor is removed,
        obtain blood pressure-related features from the converted limb BCG signal, and
        estimate a blood pressure of the user based on the blood pressure-related features.

2. The apparatus of claim 1, wherein the processor is further configured to extract the blood pressure-related features by performing beat gating on the converted limb BCG signal.

3. The apparatus of claim 2, wherein the processor is further configured to extract a representative signal from the converted limb BCG signal by performing the beat gating, and extract the blood pressure-related features from the extracted representative signal.

4. The apparatus of claim 1, wherein the processor is further configured to obtain the blood pressure-related features from the converted limb BCG signal based on a correlation between a whole-body BCG signal and the converted limb BCG signal.

5. The apparatus of claim 4, wherein the processor is further configured to, based on the sensor type and the measurement position of the BCG sensor corresponding to the acceleration sensor and the wrist of the user, obtain a J-K interval of the converted limb BCG signal as a feature related to a pulse transit time (PTT), a K-wave amplitude of the converted limb BCG signal as a feature related to aortic pulse pressure (PP), and a K-L amplitude of the converted limb BCG signal as a feature related to a distal pulse pressure (PP).

6. The apparatus of claim 1, wherein the processor is further configured to estimate the blood pressure based on the blood pressure-related features by using at least one of a linear or nonlinear regression analysis model, a neural network model, and a deep learning model.

7. The apparatus of claim 1, wherein the processor is further configured to estimate a blood pressure variation based on the blood pressure-related features, and estimate the blood pressure based on the estimated blood pressure variation and a reference blood pressure measured at a calibration time by an external blood pressure measuring device.

8. The apparatus of claim 1, further comprising:
    a pulse wave sensor configured to measure a pulse wave signal from the user,
    wherein the processor is further configured to estimate the blood pressure of the user based on the blood pressure-related features and the pulse wave signal.

9. The apparatus of claim 8, wherein the processor is further configured to:
    obtain a pulse transit time (PTT) based on a time interval between a predetermined characteristic point of the pulse wave signal and a predetermined characteristic point extracted from the limb BCG signal; and
    estimate the blood pressure based on the PTT and the blood pressure-related features.

10. A method of estimating blood pressure, the method comprising:
    measuring a limb ballistocardiogram (BCG) signal from a user, by a BCG sensor comprising an acceleration sensor;
    based on a sensor type and a measurement position of the BCG sensor, at a time when the limb BCG signal is measured, corresponding to the acceleration sensor and a wrist of the user, respectively, calibrate a reference limb BCG prediction model based on a parameter that is set according to mass of an arm with the wrist, to obtain a personalized limb BCG prediction model;
    converting, by using the personalized limb BCG prediction model that is personalized based on the sensor type and the measurement position of the BCG sensor at the time when the limb BCG signal is measured, the measured limb BCG signal to a converted limb BCG signal, in which a noise effect caused by the sensor type and the measurement position of the BCG sensor is removed;
    obtaining blood pressure-related features from the converted limb BCG signal; and
    estimating a blood pressure of the user based on the blood pressure-related features.

11. The method of claim 10, further comprising extracting characteristic points by performing beat gating on the converted limb BCG signal.

12. The method of claim 11, wherein the extracting the characteristic points comprises extracting a representative signal from the converted limb BCG signal by performing the beat gating, and extracting the characteristic points from the extracted representative signal.

13. The method of claim 10, wherein the obtaining the blood pressure-related features comprises obtaining the blood pressure-related features from the converted limb BCG signal based on a correlation between a whole-body BCG signal and the converted limb BCG signal.

14. The method of claim 13, wherein the obtaining the blood pressure-related features comprises, based on the sensor type and the measurement position of the BCG sensor corresponding to the acceleration sensor and the wrist of the user, respectively, obtaining a J-K interval of the converted limb BCG signal as a feature related to a pulse transit time (PTT), a K-wave amplitude of the converted limb BCG signal as a feature related to aortic pulse pressure (PP), and a K-L amplitude of the converted limb BCG signal as a feature related to distal pulse pressure (PP).

15. The method of claim 10, wherein the estimating the blood pressure comprises estimating the blood pressure based on the blood pressure-related features by using at least one of a linear or nonlinear regression analysis model, a neural network model, and a deep learning model.

* * * * *